(12) United States Patent
Burke et al.

(10) Patent No.: US 7,229,613 B2
(45) Date of Patent: Jun. 12, 2007

(54) METHOD FOR LOWERING SERUM GLUCOSE

(75) Inventors: Steven K. Burke, Sudbury, MA (US); Joanne M. Donovan, Needham, MA (US)

(73) Assignee: Genzyme Corporation, Cambridge, MA (US)

( * ) Notice: Subject to any disclaimer, the term of this patent is extended or adjusted under 35 U.S.C. 154(b) by 0 days.

(21) Appl. No.: 10/125,700

(22) Filed: Apr. 17, 2002

(65) Prior Publication Data

US 2002/0187121 A1     Dec. 12, 2002

Related U.S. Application Data

(60) Provisional application No. 60/305,564, filed on Jul. 13, 2001, provisional application No. 60/284,445, filed on Apr. 18, 2001.

(51) Int. Cl.
 *A61K 31/785* (2006.01)
(52) U.S. Cl. .............................. 424/78.35; 424/78.36; 424/78.37
(58) Field of Classification Search ............. 424/78.31, 424/78.16, 78.11
 See application file for complete search history.

(56) References Cited

U.S. PATENT DOCUMENTS

| | | | |
|---|---|---|---|
| 4,528,347 A | 7/1985 | Harada et al. | |
| 4,605,701 A | 8/1986 | Harada et al. | |
| 5,468,727 A | 11/1995 | Phillips et al. | |
| 5,487,888 A | 1/1996 | Mandeville, III et al. | |
| 5,496,545 A | 3/1996 | Holmes-Farley et al. | |
| 5,607,669 A | 3/1997 | Mandeville, III et al. | |
| 5,618,530 A | 4/1997 | Mandeville, III et al. | |
| 5,624,963 A | 4/1997 | Mandeville, III et al. | |
| 5,667,775 A | 9/1997 | Holmes-Farley et al. | |
| 5,679,717 A | 10/1997 | Mandeville, III et al. | |
| 5,693,675 A | 12/1997 | Mandeville, III et al. | |
| 5,702,696 A | 12/1997 | Mandeville, III et al. | |
| 5,703,188 A | 12/1997 | Mandeville, III et al. | |
| 5,900,475 A | 5/1999 | Mandeville, III et al. | |
| 5,925,379 A | 7/1999 | Mandeville, III et al. | |
| 6,083,495 A | 4/2000 | Holmes-Farley et al. | |
| 6,083,497 A | 7/2000 | Huval et al. | |
| 6,177,478 B1 | 1/2001 | Holmes-Farley et al. | |
| 6,203,785 B1 | 3/2001 | Holmes-Farley et al. | |
| 6,407,178 B1 | 6/2002 | Kolbe et al. | |
| 6,569,905 B1 * | 5/2003 | Sikorski et al. ............. | 514/661 |
| 2002/0031763 A1 | 3/2002 | Kolbe et al. | |
| 2002/0198202 A1 | 12/2002 | Gwynne et al. | |

FOREIGN PATENT DOCUMENTS

| | | |
|---|---|---|
| EP | 0 997 148 A1 | 5/2000 |
| JP | 6321787 | 11/1994 |
| WO | WO98/57652 | 12/1998 |
| WO | WO99/22743 | 5/1999 |
| WO | WO99/40990 | 8/1999 |
| WO | WO01/25291 | 4/2001 |
| WO | WO 01/25291 A1 * | 4/2001 |

OTHER PUBLICATIONS

Wizeman, W.J., and Kofinas, P., "Molecularly Imprinted Polymer Hydrogels Displaying Isomerically Resolved Glucose Binding," *Biomaterials*, 22: 1485-1491 (2001).
Garg, A., and Grundy, S.M., "Cholestyramine Therapy for Dyslipidemia in Non-Insulin Diabetes Mellitus: A Short-Term, Double-Blind, Crossover Trial," *Annals of Internal Medicine*, 121(6):416-422 (1994).
"Dietary Guidelines for Americans," *Home and Garden Bulletin No. 232* (Fifth Edition), (2000).
Clinical Study Report generated by "The SAS System," (Mar. 23, 2000).
Jones, R., "Colesevelam Hydrochloride," *Current Opinion in Cardiovascular, Pulmonary & Renal Investigational Drugs.*, 2(3):284-291(2000).
Insull, W., et al., "Colesevelam, A Novel, Potent, Polymeric Bile Acid Sequestrant Significantly Lowers LDL Cholesterol," *Presented at the 5th International Symposium on Multiple Risks Factors in Cardiovascular Disease: Global Assessment and Intervention*, Venice, Italy Oct. 28-31, 1999. (Abstract and Poster).
Ose, L., et al., "Once Per Day And Split Dosing Of Colesevelam In Patients With Type IIa Hypercholesterolemia," *Presented at the 5th International Symposium on Multiple Risks Factors in Cardiovascular Disease: Global Assessment and Intervention*, Venice, Italy Oct. 28-31, 1999. (Abstract and Poster).

(Continued)

*Primary Examiner*—Jyothsna Venkat
(74) *Attorney, Agent, or Firm*—Hamilton, Brook, Smith & Reynolds, P.C.

(57) ABSTRACT

A method for treating hyperglycemia and/or reducing serum glucose levels in a patient that includes administering to the patient a therapeutically effective amount of an amine polymer is disclosed. In one embodiment, the amine polymer is aliphatic. Examples of polymers useful in an embodiment of the invention include sevelamer hydrogen chloride and colesevelam. The invention includes the use of amine polymers such as a cross-linked polymer characterized by a repeat unit having the formula:

$$-(CH_2-CH)_n- \atop | \atop (CH_2)_x \atop | \atop NH_2 \qquad (1)$$

and salts and copolymers thereof, where n is a positive integer and x is zero or an integer between 1 and about 4. Also described is a use, for the manufacture of a medicament, of a polymer that lowers serum glucose.

4 Claims, No Drawings

OTHER PUBLICATIONS

Davidson, M.H., et al., "A New, Bile Acid Sequestrant Associated With A Low Incidence Of Gastrointestinal Side Effects," *Arch Intern Med.*, 159:1893-1900(1999).

Mesner, C.H., et al., "Effect Of Cholestagel And Lovastatin Alone And In Combination For The Treatment Of Hypercholesterolemia," *Presented at the XIII International Symposium On Drugs Affecting Lipid Metabolism,* Florence, Italy; May 30, 1998-Jun. 3, 1998. (Abstract).

Heller D., et al., "Absorption of $^{14}$C-Colesevelam Hydrochloride In Normal Volunteers," *Presented at the 1999 AAPS Annual Meeting And Exposition.* New Orleans, LA. Nov. 14-18, 1999. (Abstract).

Declaration Of Joanne Donovan Under 37 C.F.R. 1.132.

"Welchol™ Tablets Package Insert", *Center for Drug Evaluation and Research*, Application Number: NDA 21-176, pp. 1-11, and NDA 21-141, pp. 1-11.

"Renagel® Package Insert", *GelTex Pharmaceuticals, Inc.*, Waltham, Massachusetts, 4712 (Jul. 2000), Issued XX/00, pp. 1-10.

Dennis I. Goldberg, et al.,"Effect of RenaGel®, a non-absorbed, calcium-and aluminium-free phosphate binder, on serum phosphorus, calcium, and intact parathyroid hormone in end-stage renal disease patients," *Nephrol Dial Transplant*, 13:2303-2310, (1998).

Glenn M. Chertow, MD, MPH, et al., "Poly [allylamine Hydrochloride] (RenaGel): A Noncalcemic Phosphate Binder for the Treatment of Hyperphosphatemia in Chronic Renal Failure," *American Journal of Kidney Diseases*, vol. 29, No. 1, pp. 66-71, (1997).

G.M. Chertow, et al., "A Randomized trial of sevelamer hydrochloride (RenaGel) with and without supplemental calcium," *Clinical Nephrology*, vol. 51, No. 1, pp. 18-26, (1999).

Anthony J. Bleyer, MD, MS, et al., "A Comparison of the Calcium-Free Phosphate Binder Sevelamer Hydrochloride With Calcium Acetate in the Treatment of Hyperphosphatemia in Hemodialysis Patients," *American Journal of Kidney Diseases*, vol. 33, No. 4, pp. 694-701, (1999).

Eduardo A. Slatopolsky, et al., "RenaGel®, a nonabsorbed calcium-and aluminum-free phosphate binder, lowers serum phosphorus and parathyroid hormone," *Kidney International*, vol. 55, pp. 299-307, (1999).

Glenn M. Chertow, et al., "Long-term effects of sevelamer hydrochloride on the calcium x phosphate product and lipid profile of haemodialysis patients," *Nephrol Dial Transplant*, 14:2907-2914, (1999).

G.M. Chertow, et al., "Hyperparathyroidism and dialysis vintage," *Clinical Nephrology* vol. 54, No. 4, pp. 295-300, (2000).

Steven K. Burke, "RenaGel®: reducing serum phosphorus in haemodialysis patients," *Reprinted from Hospital Medicine*, vol. 61, No. 9, (2000).

Glenn M. Chertow, et al., "Sevelamer attenuates the progression of coronary and aortic calcification in hemodialysis patients," *Kidney International*, vol. 62, pp. 245-252, (2002).

Glenn M. Chertow, MD, MPH, et al., "Sevelamer With and Without Calcium and Vitamin D: Observations From a Long-Term Open-Label Clinical Trial," *Journal of Renal Nutrition*, vol. 10, No. 3, pp. 125-132, (2000).

A.J. Collins, et al., "Hospitalization risks between Renagel phosphate binder treated and non-Renagel treated patients," *Clinical Nephrology*, vol. 54, No. 4, pp. 334-341, (2000).

B.M. Wilkes, et al., "Simultaneous lowering of serum phosphate and LDL-cholesterol by sevelamer hydrochloride (RenaGel) in dialysis patients," *Clinical Nephrology*, vol. 50, No. 6, pp. 381-386, (1998).

"Welchol™ Tablets Package Insert", *Center for Drug Evaluation and Research*, Application Number: NDA 21-176, pp. 1-11, and NDA 21-141, pp. 1-11, May 2000.

"Renagel® Package Insert", *GelTex Pharmaceuticals, Inc.*, Waltham, Massachusetts, 4712 (Jul. 2000), Issued XX/00, pp. 1-10.

Dennis I. Goldberg, et al., "Effect of RenaGel®, non-absorbed, calcium-and aluminium-free phosphate binder, on serum phosphorus, calcium, and intact parathyroid hormone in end-stage renal disease patients," *Nephrol Dial Transplant*, 13:2303-2310, (1998).

Glenn M. Chertow, MD, MPH, et al., "Poly [allylamine Hydrochloride] (RenaGel): A Noncalcemic Phosphate Binder for the Treatment of Hyperphosphatemia in Chronic Renal Failure," *American Journal of Kidney Diseases*, vol. 29, No. 1, pp. 66-71, (1997).

G.M. Chertow, et al., "A Randomized trial of sevelamer hydrochloride (RenaGel) with and without supplemental calcium," *Clinical Nephrology*, vol. 51, No. 1, pp. 18-26, (1999).

Anthony J. Bleyer, MD, MS, et al., "A Comparison of the Calcium-Free Phosphate Binder Sevelamer Hydrochloride With Calcium Acetate in the Treatment of Hyperphosphatemia in Hemodialysis Patients," *American Journal of Kidney Diseases*, vol. 33, No. 4, pp. 694-701, (1999).

Eduardo A. Slatopolsky, et al, "RenaGel®, a nonabsorbed calcium-and aluminum-free phosphate binder, lowers serum phosphorus and parathyroid hormone," *Kidney International*, vol. 55, pp. 299-307, (1999).

Glenn M. Chertow, et al., "Long-term effects of sevelamer hydrochloride on the calcium x phosphate product and lipid profile of haemodialysis patients,"*Nephrol Dial Transplant*, 14:2907-2914, (1999).

G.M. Chertow, et al., "Hyperparathyroidism and dialysis vintage," *Clinical Nephrology* vol. 54, No. 4, pp. 295-300, (2000).

Steven K. Burke, "RenaGel®: reducing serum phosphorus in haemodialysis patients," *Reprinted from Hospital Medicine*, vol. 61, No. 9, (2000).

Glenn M. Chertow, et al., "Sevelamer attenuates the progression of coronary and aortic calcification in hemodialysis patients," *Kidney International*, vol. 62, pp. 245-252, (2002).

\* cited by examiner

METHOD FOR LOWERING SERUM GLUCOSE

RELATED APPLICATIONS

This application claims the benefit of U.S. Provisional Application No. 60/305,564, filed on Jul. 13, 2001, and U.S. Provisional Application No. 60/284,445, filed on Apr. 18, 2001.

The entire teachings of the above applications are incorporated herein by reference.

BACKGROUND OF THE INVENTION

Nondiabetic hyperglycemia (high blood glucose concentration) is an indicator of cardiovascular risk (Balkan, B. et al., 21 *Diabetes Care*, 360 (1998)). About 16 million Americans have type 2 diabetes. Individuals with both type 2 and type 1 diabetes have elevated blood sugar levels due to insulin regulation problems. Individuals with diabetes who practice tight blood glucose control can substantially reduce the risk of developing vascular complications of diabetes, including diabetic retinopathy (a condition which leads to blindness), diabetic nephropathy, diabetic neuropathy, and atherosclerosis.

Current methods of controlling blood glucose concentration include insulin injections, oral administration of sulfonylureas, glucophage (a biguanide drug), alpha-glucosidase inhibitors, and thiazolidinedione. Some of these therapies have serious side-effects.

SUMMARY OF THE INVENTION

The present invention relates to the discovery that aliphatic amine polymers, such as sevelamer hydrogen chloride and colesevelam, lower serum glucose levels upon administration to the gastrointestinal tract. As such, the invention relates to a treatment for high blood glucose levels with a polymer that binds to glucose, or otherwise lowers serum glucose-levels, such as a polymer that possesses a glucose-level lowering effect as an indirect result upon administration, (i.e., not dependent upon glucose-binding). One embodiment of the invention includes a treatment for reducing serum glucose levels in individuals with diabetes; another embodiment includes a treatment for non-diabetic individuals with hyperglycemia.

The invention includes the use of polymers which bind glucose and precursors of glucose, preventing its absorption (or reabsorption), or which otherwise cause a serum glucose-lowering effect. Functional groups that can bind to glucose can be attached to a polymer backbone, the polymer preferably of sufficient molecular weight to prevent absorption.

In one preferred embodiment the polymer is a cross-linked polyamine. The cross-linking avoids or minimizes absorption of the polymer in the patient. Such polyamines can include aliphatic amine polymers such as, polyallylamine, polydiallylamine, polyethyleneimine (linear or branched), polyvinylamine, polybutenylamine, polylysine, polyarginine, and poly(aminopropylacrylamide). The polyamines can also include aromatic amine polymers such as cholestyramine.

Preferred polymers employed in the invention comprise water-insoluble, non-absorbable, and cross-linked polyamines as described herein. The polyamines of the invention can be amine or ammonium-containing aliphatic polymers. An aliphatic amine polymer, is a polymer which contains aliphatic amine moieties. In a preferred embodiment, the polymers are characterized by one or more monomeric units of Formula I:

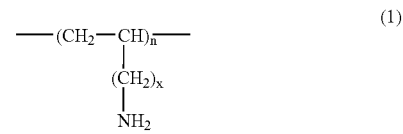

and salts thereof, where n is a positive integer and x is 0 or an integer between 1 and about 4, preferably 1. In preferred embodiments, the polymer is cross-linked by means of a multifunctional cross-linking agent.

The invention provides an effective treatment for reducing high levels of glucose in the blood. The invention also provides for the use of the polymers described herein for the manufacture of a medicament for the treatment of hyperglycemia.

Other features and advantages will be apparent from the following description of the preferred embodiments thereof and from the claims.

DETAILED DESCRIPTION OF THE INVENTION

As described above, the preferred polymers employed in the invention comprise water-insoluble, non-absorbable, cross-linked polyamines. Preferred polymers are aliphatic. Examples of preferred polymers include polyethyleneimine, polyallylamine, polyvinylamine and polydiallylamine polymers. The polymers can be homopolymers or copolymers, as discussed below, and can be substituted or unsubstituted. These and other polymers which can be used in the claimed invention have been reported in U.S. Pat. Nos. 5,487,888; 5,496,545; 5,607,669; 5,618,530; 5,624,963; 5,667,775; 5,679,717; 5,703,188; 5,702,696 and 5,693,675, the contents of which are hereby incorporated herein by reference in their entireties. Polymers suitable for use in the invention are also reported in copending U.S. application Ser. Nos. 08/659,264 (now U.S. Pat. No. 5,900,475); 08/823,699 (now abandoned); 08/835,857 (now abandoned); 08/470,940 (now abandoned); 08/826,197 (now U.S. Pat. No. 5,925,379); 08/777,408 (now U.S. Pat. No. 6,203,785); 08/927,247 (now abandoned); 08/964,498 (now abandoned); 08/964,536 (now U.S. Pat. No. 6,083,497) and 09/359,226 (now U.S. Pat. No. 6,177,478), the contents of which are incorporated herein by reference in their entireties.

The polymer can be a homopolymer or a copolymer of one or more amine-containing monomers or a copolymer of one or more amine-containing monomers in combination with one or more non-amine containing monomers. Where copolymers are manufactured with the monomer of the above Formula I, the comonomers are preferably inert and non-toxic. Examples of suitable non-amine-containing monomers include vinylalcohol, acrylic acid, acrylamide, and vinylformamide. Examples of amine-containing monomers preferably include monomers having the Formula 1 above. Preferably, the monomers are aliphatic. Most preferably, the polymer is a homopolymer, such as a homopolyallylamine, homopolyvinylamine, homopolydiallylamine or polyethylenamine. The term "amine," as used herein, includes primary, secondary and tertiary amines, as well as ammoniums such as trialkylammonium, and guanidino groups.

Other preferred polymers include polymers characterized by one or more repeat units set forth below.

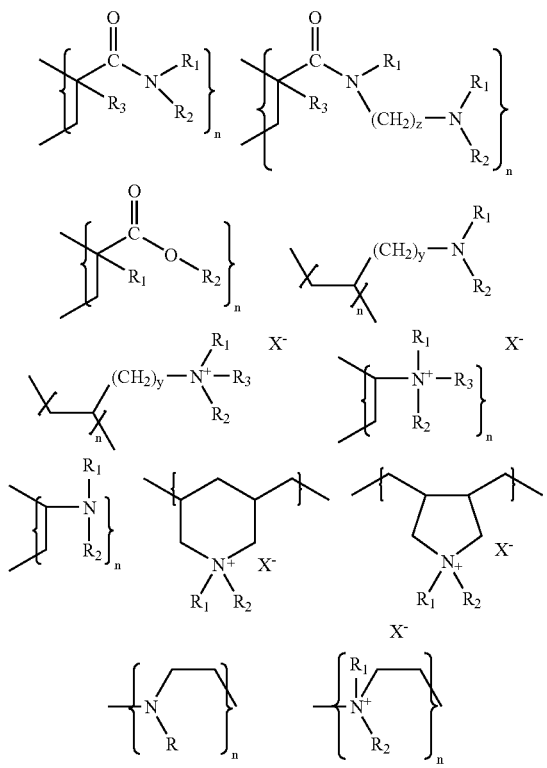

or copolymers thereof, wherein n is a positive integer, y and z are both integers of one or more (e.g., between about one and about 10) and each R, $R_1$, $R_2$, and $R_3$, independently, is H, or a substituted or unsubstituted alkyl group (e.g., having between 1 and 25 or between 1 and 5 carbon atoms, inclusive), alkylamino, (e.g., having between 1 and 5 carbons atoms, inclusive, such as ethylamino or poly(ethylamino)) or aryl (e.g., phenyl) group, and each $X^-$ is an exchangeable negatively charged counterion.

In one preferred polymer, at least one of R, $R_1$, $R_2$, or $R_3$ groups is a hydrogen atom. In a more preferred embodiment, each of these groups are hydrogen.

In each case, the R groups can carry one or more substituents. Suitable substituents include therapeutic cationic groups, e.g., quaternary ammonium groups, or amine groups, e.g., primary, secondary or tertiary alkyl or aryl amines. Examples of other suitable substituents include hydroxy, alkoxy, carboxamide, sulfonamide, halogen, alkyl, aryl, hydrazine, guanidine, urea, poly(alkyleneimine), such as poly(ethyleneimine), and carboxylic acid esters.

Preferably, the polymer is rendered water-insoluble by cross-linking. The cross-linking agent can be characterized by functional groups which react with the amino group of the monomer. Alternatively, the cross-linking group can be characterized by two or more vinyl groups which undergo free radical polymerization with the amine monomer.

Examples of suitable cross-linking agents include diacrylates and dimethylacrylates (e.g. ethylene glycol diacrylate, propylene glycol diacrylate, butylene glycol diacrylate, ethylene glycol dimethacrylate, propylene glycol dimethacrylate, butylene glycol dimethacrylate, polyethyleneglycol dimethacrylate and polyethyleneglycol diacrylate), methylene bisacrylamide, methylene bismethacrylamide, ethylene bisacrylamide, ethylene bismethacrylamide, ethylidene bisacrylamide, divinylbenzene, bisphenol A, dimethacrylate and bisphenol A diacrylate. The cross-linking agent can also include acryloyl chloride, epichlorohydrin, butanediol diglycidyl ether, ethanediol diglycidyl ether, succinyl dichloride, the diglycidal ether of bisphenol A, pyromellitic dianhydride, toluene diisocyanate, ethylene diamine and dimethyl succinate.

Preferably the polymer is non-absorbable in the gastrointestinal tract and/or substantially water-insoluble. The polymer can be characterized by 10 or more monomeric units and/or possess a molecular weight of about 570 or more, preferably about 5,000 daltons or more.

The terms "insoluble," "substantially water-insoluble," and grammatical variations thereof, as used herein, refer to a polymer or other substance which does not dissolve in an aqueous-based system, or which dissolves or solubilizes at a slower rate than does a water-soluble substance. Water-insoluble polymers introduced into the gastrointestinal tract are not absorbed systemically, or are absorbed to a lesser extent than are water-soluble polymers.

"Nonabsorbent" or "non-absorbable," as the terms are used herein, means that the polymer or other substance so described does not dissolve in the gastrointestinal tract, or dissolves to a lesser extent than does an absorbent or absorbable substance, or does not erode, degrade, or otherwise break down in vitro to form smaller chemical species by either physical or chemical processes. Therefore, a non-absorbable polymer is not absorbed systemically or is absorbed to a lesser extent than is an absorbable polymer.

A preferred cross-linking agent is epichlorohydrin because of its high availability and low cost. Epichlorohydrin is also advantageous because of its low molecular weight and hydrophilic nature, increasing the water-swellability and gel properties of the polyamine.

The level of cross-linking makes the polymers insoluble and substantially resistant to absorption and degradation, thereby limiting the activity of the polymer to the gastrointestinal tract, and reducing potential side-effects in the patient. The compositions thus tend to be non-systemic in activity. Typically, the cross-linking agent is present in an amount from about 0.5–35% or about 0.5–25% (such as from about 2.5–20% or about 1–10%) by weight, based upon total weight of monomer plus cross-linking agent. The polymers can also be further derivatized; examples include alkylated amine polymers, as described, for example, in U.S. Pat. Nos. 5,679,717, 5,607,669 and 5,618,530, the teachings of which are incorporated herein by reference in their entireties. Preferred alkylating agents include hydrophobic groups (such as aliphatic hydrophobic groups) and/or quaternary ammonium- or amine-substituted alkyl groups.

Non-cross-linked and cross-linked polyallylamine and polyvinylamine are generally known in the art and are commercially available. Methods for the manufacture of polyallylamine and polyvinylamine, and cross-linked derivatives thereof, are described in the above US Patents. Harada et al. (U.S. Pat. Nos. 4,605,701 and 4,528,347), which are incorporated herein by reference in their entireties, also describe methods of manufacturing polyallylamine and cross-linked polyallylamine.

In other embodiments, the polymer can be a homopolymer or copolymer of polybutenylamine, polylysine, or polyarginine. Alternatively, the polymer can be an aromatic polymer, such as an amine or ammonium-substituted polystyrene, (e.g., cholestyramine).

As described above the polymer can be administered in the form of a salt. By "salt" it is meant that the nitrogen group in the repeat unit is protonated to create a positively charged nitrogen atom associated with a negatively charged counterion. A preferred polymer is a low salt, such as low chloride, form of polyallylamine where less than 40% of the amine groups are protonated.

The cationic counterions can be selected to minimize adverse effects on the patient, as is more particularly described below. Examples of suitable counterions include organic ions, inorganic ions, or a combination thereof, such as halides ($Cl^-$ and $Br^-$), $CH_3OSO_3^-$, $HSO_4^-$, $SO_4^{2-}$, $HCO_3^-$, $CO_3^-$, acetate, lactate, succinate, propionate, oxalate, butyrate, ascorbate, citrate, dihydrogen citrate, tartrate, taurocholate, glycocholate, cholate, hydrogen citrate, maleate, benzoate, folate, an amino acid derivative, or a lipid. The counterions can be the same as, or different from, each other. For example, the polymer can contain two different types of counterions.

The polymers, according to an embodiment of the invention, are administered to a patient in a therapeutically effective amount. As used herein, the terms "therapeutically effective amount" and "therapeutically effective dose" refer to the amount of an active agent, for example, a therapeutically effective substance, such as a polymer described herein, required to be administered in order to induce a desired result in the patient. That result may be alleviation or amelioration (complete or partial) of the symptoms or condition of the patient in need of treatment, or any other desired improvement in the patient's symptoms, disease or condition.

As used herein, the term "therapeutically effective amount" may also refer to the quantity of active agent or therapeutically effective substance, such as an amine polymer described herein, the administration of which results in improvement in the patient's symptoms, disease, or condition, where little or no improvement would occur in the absence of the active agent. Typically, the polymer is administered for a sufficient period of time to achieve the desired therapeutic effect.

Therapeutic efficacy may be determined by using standard pharmacological procedures in experimental animals.

The polymers according to the invention can be administered to the gastrointestinal tract in a dosage comprising between about 1 μg/kg/day and about 1 g/kg/day. The particular dosage will depend on the individual patient (e.g., the patient's weight and the extent of glucose removal required) and on the nature of the polymer used. Polymers according to the invention can be administered in one or several doses per day. In one embodiment, it is presently contemplated that, for therapeutic treatments, at least one polymer of the present invention can be administered to an adult in an amount comprising between about 70 μg and about 91 g per day; between about 0.1 g and about 10 g per day; between about 0.5 g and about 6 g per day; or between about 0.5 g and about 3 g per day. The polymer can be administrated either in hydrated or dehydrated form, and can be flavored or added to a food or drink, if desired, to enhance patient acceptability. A preferred adult dose is between about 3 g and about 6 g per day. The polymer is preferably given with food.

Additional ingredients such as ingredients for treating other related indications, or inert ingredients, such as artificial coloring agents can be added as well.

The additional active ingredients can be administered simultaneously or sequentially with the polymer. Where the ingredients are administered simultaneously, they can optionally be bound to the polymer, for example, by covalent bonding or by physically encapsulating the ingredient, on the exterior or interior of the polymeric particle. Covalent bonding can be accomplished by reacting the polymer and ingredient(s) with suitable cross-linking agents. For example, polyallylamine and penicillamine can be cross-linked via hydrolyzable bond.

Examples of suitable forms for administration (preferably oral administration) include pills, tablets, capsules, and powders (e.g., for sprinkling on food or incorporating into a drink). The pill, tablet, capsule, or powder can be coated with a substance capable of protecting the composition from disintegration in the esophagus but will allow disintegration as the composition in the stomach and mixing with food to pass into the patient's small intestine. The polymer can be administered alone or in combination with a pharmaceutically acceptable carrier substance, e.g., zinc salts or magnesium carbonate, with which the polymer can form a micelle.

The polymers of the invention can be used to treat patients, preferably humans, with high glucose levels, or as a prophylactic.

EXEMPLIFICATION

A. Polymer Preparation

EXAMPLE 1

Poly(vinylamine)

The first step involved the preparation of ethylidenebisacetamide. Acetamide (118 g), acetaldehyde (44.06 g), glucose acetate (0.2 g), and water (300 mL) were placed in a 1 L three neck flask fitted with condenser, thermometer, and mechanically stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes, after which the solid was filtered off and discarded. The acetone was cooled to 0° C. and solid was filtered off. The solid was rinsed in 500 mL acetone and air dried 18 hours to yield 31.5 g of ethylidenebisacetamide.

The next step involved the preparation of vinylacetamide from ethylidenebisacetamide. Ethylidenebisacetamide (31.05 g), calcium carbonate (2 g) and filter agent, Celite® 541 (2 g) (available from Aldrich, Milwaukee, Wis.) were placed in a 500 mL three neck flask fitted with a thermometer, a mechanical stirrer, and a distilling head atop a Vigreaux column. The mixture was vacuum distilled at 24 mm Hg by heating the pot to 180–225° C. Only a single fraction was collected (10.8 g) which contained a large portion of acetamide in addition to the product (determined by NMR). This solid product was dissolved in isopropanol (30 mL) to form the crude vinylacetamide solution used for polymerization.

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven at about room temperature to yield 0.8 g of poly(vinylacetamide), which was used to prepare poly(vinylamine) as follows.

Poly(vinylacetamide) (0.79 g) was placed in a 100 mL one neck flask containing water (25 mL) and conc. HCl (25 mL). The mixture was refluxed for 5 days, after which the solid was filtered off, rinsed once in water, twice in isopropanol, and dried in a vacuum oven to yield 0.77 g of product. Infrared spectroscopy indicated that a significant amount of the amide (1656 cm$^{-1}$) remained and that not much amine (1606 cm$^{-1}$) was formed. The product of this reaction (~0.84 g) was suspended in NaOH (46 g) and water (46 g) and heated to boiling (~140° C.). Due to foaming the temperature was reduced and maintained at ~100° C. for 2 hours. Water (100 mL) was added and the solid collected by filtration. After rinsing once in water the solid was suspended in water (500 mL) and adjusted to pH 5 with acetic acid. The solid was again filtered off, rinsed with water, then isopropanol, and dried in a vacuum oven to yield 0.51 g of product. Infrared spectroscopy indicated that significant amine had been formed.

EXAMPLE 2

Poly(allylamine)Hydrochloride

To a 2 liter, water-jacketed reaction kettle equipped with (1) a condenser topped with a nitrogen gas inlet, (2) a thermometer, and (3) a mechanical stirrer was added concentrated hydrochloric acid (360 mL). The acid was cooled to 5° C. using circulating water in the jacket of the reaction kettle (water temperature=0° C.). Allylamine (328.5 mL, 250 g) was added dropwise with stirring while maintaining the reaction temperature at 5–10° C. After addition was complete, the mixture was removed, placed in a 3 liter one-neck flask, and 206 g of liquid was removed by rotary vacuum evaporation at 60° C. Water (20 mL) was then added and the liquid was returned to the reaction kettle. Azobis (amidinopropane) dihydrochloride (0.5 g) was suspended in 11 mL of water was then added. The resulting reaction mixture was heated to 50° C. under a nitrogen atmosphere with stirring for 24 hours. Additional azobis(amidinopropane) dihydrochloride (5 mL) suspended in 11 mL of water was then added, after which heating and stirring were continued for an additional 44 hours.

At the end of this period, distilled water (100 mL) was added to the reaction mixture and the liquid mixture allowed to cool with stirring. The mixture was then removed and placed in a 2 liter separatory funnel, after which it was added dropwise to a stirring solution of methanol (4 L), causing a solid to form. The solid was removed by filtration, re-suspended in methanol (4 L), stirred for 1 hour, and collected by filtration. The methanol rinse was then repeated one more time and the solid dried in a vacuum oven at about room temperature to afford 215.1 g of poly(allylamine) hydrochloride as a granular white solid.

EXAMPLE 3

Poly(allylamine) Hydrochloride Cross-Linked with Epichlorohydrin

To a 5 gallon vessel was added poly(allylamine) hydrochloride prepared as described in Example 2 (1 kg) and water (4 L). The mixture was stirred to dissolve the hydrochloride and the pH was adjusted by adding solid NaOH (284 g). The resulting solution was cooled to room temperature, after which epichlorohydrin cross-linking agent (50 mL) was added all at once with stirring. The resulting mixture was stirred gently until it gelled (about 35 minutes). The cross-linking reaction was allowed to proceed for an additional 18 hours at room temperature, after which the polymer gel was removed and placed in portions in a blender with a total of 10 L of water. Each portion was blended gently for about 3 minutes to form coarse particles which were then stirred for 1 hour and collected by filtration. The solid was rinsed three times by suspending it in water (10 L, 15 L, 20 L), stirring each suspension for 1 hour, and collecting the solid each time by filtration. The resulting solid was then rinsed once by suspending it in isopropanol (17 L), stirring the mixture for 1 hour, and then collecting the solid by filtration, after which the solid was dried in a vacuum oven at 50° C. for 18 hours to yield about 677 g of the cross-linked polymer as a granular, brittle, white solid.

EXAMPLE 4

Poly(allylamine) Hydrochloride Cross-Linked with Butanediol Diglycidyl Ether To a 5 gallon plastic bucket was added poly(allylamine) hydrochloride prepared as described in Example 2 (500 g) and water (2 L). The mixture was stirred to dissolve the hydrochloride and the pH was adjusted to 10 by adding solid NaOH (134.6 g). The resulting solution was cooled to room temperature in the bucket, after which 1,4-butanediol diglycidyl ether cross-linking agent (65 mL) was added all at once with stirring. The resulting mixture was stirred gently until it gelled (about 6 minutes). The cross-linking reaction was allowed to proceed for an additional 18 hours at room temperature, after which the polymer gel was removed and dried in a vacuum oven at 75° C. for 24 hours. The dry solid was then ground and sieved to –30 mesh, after which it was suspended in 6 gallons of water and stirred for 1 hour. The solid was then filtered off and the rinse process repeated two more times. The resulting solid was then air dried for 48 hours, followed by drying in a vacuum oven at 50° C. for 24 hours to yield about 415 g of the cross-linked polymer as a white solid.

EXAMPLE 5

Poly(allylamine) Hydrochloride Cross-linked with Ethanediol Diglycidyl Ether To a 100 mL beaker was added poly(allylamine) hydrochloride prepared as described in Example 2 (10 g) and water (40 mL). The mixture was stirred to dissolve the hydrochloride and the pH was adjusted to 10 by adding solid NaOH. The resulting solution was cooled to room temperature in the beaker, after which 1,2-ethanediol diglycidyl ether cross-linking agent (2.0 mL) was added all at once with stirring. The resulting mixture was stirred gently until it gelled (about 4 minutes). The cross-linking reaction was allowed to proceed for an additional 18 hours at room temperature, after which the polymer gel was removed and blended in 500 mL of methanol. The solid was then filtered off and suspended in water (500 mL). After stirring for 1 hour, the solid was filtered off and the rinse process repeated. The resulting solid was rinsed twice in isopropanol (400 mL) and then dried in a vacuum oven at 50° C. for 24 hours to yield 8.7 g of the cross-linked polymer as a white solid.

EXAMPLE 6

Poly(allylamine) Hydrochloride Cross-linked with Dimethylsuccinate

To a 500 mL round bottom flask was added poly(allylamine) hydrochloride prepared as described in Example 2 (10 g), methanol (100 mL), and triethylamine (10 mL). The mixture was stirred and dimethylsuccinate cross-linking agent (1 mL) was added. The solution was heated to reflux and the stirring discontinued after 30 minutes. After 18 hours, the solution was cooled to room temperature, and the solid filtered off and blended in 400 mL of isopropanol. The solid was then filtered off and suspended in water (1 L). After stirring for 1 hour, the solid was filtered off and the rinse process repeated two more times. The solid was then rinsed once in isopropanol (800 mL) and dried in a vacuum oven at 50° C. for 24 hours to yield 5.9 g of the cross-linked polymer as a white solid.

EXAMPLE 7

Poly(allyltrimethylammonium Chloride)

To a 500 mL three-necked flask equipped with a magnetic stirrer, a thermometer, and a condenser topped with a nitrogen inlet, was added poly(allylamine) cross-linked with epichlorohydrin (5.0 g), methanol (300 mL), methyl iodide (20 mL), and sodium carbonate (50 g). The mixture was then cooled and water was added to total volume of 2 L. Concentrated hydrochloric acid was added until no further bubbling resulted and the remaining solid was filtered off. The solid was rinsed twice in 10% aqueous NaCl (1 L) by stirring for 1 hour followed by filtration to recover the solid. The solid was then rinsed three times by suspending it in water (2 L), stirring for 1 hour, and filtering to recover the solid. Finally, the solid was rinsed as above in methanol and dried in a vacuum over at 50° C. for 18 hours to yield 7.7 g of white granular solid.

EXAMPLE 8

Poly(ethyleneimine)/Acryloyl Chloride

Into a 5 L three-neck flask equipped with a mechanical stirrer, a thermometer, and an additional funnel was added polyethyleneimine (510 g of a 50% aqueous solution (equivalent to 255 g of dry polymer) and isopropanol (2.5 L). Acryloyl chloride (50 g) was added dropwise through the addition funnel over a 35 minute period, keeping the temperature below 29° C. The solution was then heated to 60° C. with stirring for 18 hours. The solution was cooled and solid immediately filtered off. The solid was rinsed three times by suspending it in water (2 gallons), stirring for 1 hour, and filtering to recover the solid. The solid was rinsed once by suspending it in methanol (2 gallons), stirring for 30 minutes, and filtering to recover the solid. Finally, the solid was rinsed as above in isopropanol and dried in a vacuum over at 50° C. for 18 hours to yield 206 g of light orange granular solid.

EXAMPLE 9

Poly(dimethylaminopropylacrylamide)

Dimethylamino-propylacrylamide (10 g) and methylene-bisacrylamide (1.1 g) were dissolved in 50 mL of water in a 100 mL three-neck flask. The solution was stirred under nitrogen for 10 minutes. Potassium persulfate (0.3 g) and sodium metabisulfite (0.3 g) were each dissolved in 2–3 mL of water and then mixed. After a few seconds this solution was added to the monomer solution, still under nitrogen. A gel formed immediately and was allowed to sit overnight. The gel was removed and blended with 500 mL of isopropanol. The solid was filtered off and rinsed three times with acetone. The solid white powder was filtered off and dried in a vacuum oven at about room temperature to yield 6.1 g.

EXAMPLE 10

Poly(Methacrylamidopropyltrimethy-lammoniumchloride)=(Poly(MAPTAC))

(3-(Methacryloylamino)propyl)trimethylammonium chloride (38 mL of 50% aqueous solution) and methyl-enebis-methacrylamide (2.2 g) were stirred in a beaker at room temperature. Methanol (10 mL) was added and the solution was warmed to 40° C. to fully dissolve the bisacrylamide. Potassium persulfate (0.4 g) was added and the solution stirred for 2 minutes. Potassium metabisulfite (0.4 g) was added and stirring was continued. After 5 minutes the solution was put under a nitrogen atmosphere. After 20 minutes the solution contained significant precipitate and the solution was allowed to sit overnight. The solid was washed three times with isopropanol and collected by filtration. The solid was then suspended in water 500 (mL) and stirred for several hours before being collected by centrifugation. The solid was again washed with water and collected by filtration. The solid was then dried in a vacuum oven at about room temperature to yield 21.96 g.

EXAMPLE 11

Poly(ethyleneimine) "A"

Polyethyleneimine (50 g of a 50% aqueous solution; Scientific Polymer Products) was dissolved in water (100 mL). Epichlorohydrin (4.6 mL) was added dropwise. The solution was heated to 55° C. for 4 hours, after which it had gelled. The gel was removed, blended with water (1 L) and the solid was filtered off. It was resuspended in water (2 L) and stirred for 10 minutes. The solid was filtered off, the rinse repeated once with water and twice with isopropanol, and the resulting gel was dried in a vacuum oven at about room temperature to yield 26.3 g of a rubbery solid.

Poly(ethyleneimine) "B" and Poly(ethyleneimine) "C" were made in a similar manner, except using 9.2 and 2.3 mL of epichlorohydrin, respectively.

EXAMPLE 12

Poly(methylmethacrylate-co-divinylbenzene)

Methylmethacrylate (50 g) and divinylbenzene (5 g) and azobisisobutyronitrile (1.0 g) were dissolved in isopropanol (500 mL) and heated to reflux for 18 hours under a nitrogen 14 atmosphere. The solid white precipitate was filtered off, rinsed once in acetone (collected by centrifugation), once in water (collected by filtration) and dried in a vacuum oven at about room temperature to yield 19.4 g.

EXAMPLE 13

Poly(diethylenetriaminemethacrylamide)

Poly(methyl-methacrylate-co-divinylbenzene) (20 g) was suspended in diethylenetriamine (200 mL) and heated to reflux under a nitrogen atmosphere for 18 hours. The solid was collected by filtration, resuspended in water (500 mL), stirred 30 minutes, filtered off, resuspended in water (500 mL), stirred 30 minutes, filtered off, rinsed briefly in isopropanol, and dried in a vacuum oven at about room temperature to yield 18.0 g.

Poly(pentaethylenehexaminemethacrylamide), Poly(tetraethylenepentaminemethacrylamide), and Poly(triethylene-tetraaminemethacrylamide) were made in a manner similar to poly(diethylenetriaminemethacrylamide) from pentaethylenehexamine, tetraethylenepentamine, and triethylenetetraamine, respectively.

EXAMPLE 14

Poly(methylmethacrylate/PEI)

Poly(methylmethacrylate-co-divinylbenzene) (1.0 g) was added to a mixture containing hexanol (9150 mL) and polyethyleneimine (15 g in 15 g water). The mixture was heated to reflux under nitrogen for 4 days. The reaction was cooled and the solid was filtered off, suspended in methanol (300 mL), stirred 1 hour, and filtered off. The rinse was repeated once with isopropanol and the solid was dried in a vacuum oven at about room temperature to yield 0.71 g.

EXAMPLE 15

Poly(aminoethylmethacrylamide)

Poly(methylmethacrylate-co-divinylbenzene) (20 g) was suspended in ethylenediamine 9200 mL) and heated to reflux under a nitrogen atmosphere for 3 days. The solid was collected by centrifugation, washed by resuspending it in water (500 mL), stirring for 30 minutes, and filtering off the solid. The solid was washed twice more in water, once in isopropanol, and dried in a vacuum oven at about room temperature to yield 17.3 g.

EXAMPLE 16

Poly(diethylaminopropylmethacrylamide)

Poly(methyl-methacrylate-co-divinylbenzene) (20 g) was suspended in diethylaminopropylamine (200 mL) and heated to reflux under a nitrogen atmosphere for 18 hours. The solid was collected by filtration, resuspended in water (500 mL), filtered off, resuspended in water (500 mL), collected by filtration, rinsed briefly in isopropanol, and dried in a vacuum oven at about room temperature to yield 8.2 g.

EXAMPLE 17

NHS-acrylate

N-Hydroxysuccinimide (NHS, 157.5 g) was dissolved in chloroform (2300 mL) in a 5 L flask. The solution was cooled to 0° C. and acryloyl chloride (132 g) was added dropwise, keeping the temperature at 2° C. After addition was complete, the solution was stirred for 1.5 hours, rinsed with water (1100 mL) in a separatory funnel and dried over anhydrous sodium sulfate. The solvent was removed under vacuum, and a small amount of ethyl acetate was added to the residue. This mixture was poured into hexane (200 mL) with stirring. The solution was heated to reflux, adding more ethyl acetate (400 mL). The insoluble NHS was filtered off, hexane (1 L) was added, the solution was heated to reflux, ethyl acetate (400 mL) was added, and the solution allowed to cool to <10° C. The solid was then filtered off and dried in a vacuum oven at about room temperature to yield 125.9 g. A second crop of 80 g was subsequently collected by further cooling.

EXAMPLE 18

Poly(NHS-acrylate)

NHS-acrylate (28.5 g), methylenebis-acrylamide (1.5 g) and tetrahydrofuran (500 mL) were mixed in a 1 L flask and heated to 50° C. under a nitrogen atmosphere. Azobisisobutyronitrile (0.2 g) was added, the solution was stirred for 1 hour, filtered to remove excess N-hydroxysuccinimide, and heated to 50° C. for 4.5 hours under a nitrogen atmosphere. The solution was then cooled and the solid was filtered off, rinsed in tetrahydrofuran, and dried in a vacuum oven at about room temperature to yield 16.1 g.

EXAMPLE 19

Poly(guanidinobutylacrylamide)

Poly(NHS-acrylate) (1.5 g) was suspended in water (25 mL) containing agmatine (1.5 g) which had been adjusted to pH 9 with solid NaOH. The solution was stirred for 4 days, after which time the pH had dropped to 6.3. Water was added to a total of 500 mL, the solution was stirred for 30 minutes and the solid was filtered off. The solid was rinsed twice in water, twice in isopropanol, and dried in a vacuum oven at about room temperature to yield 0.45 g.

EXAMPLE 20

Poly(methacryloyl Chloride)

Methacryloyl chloride (20 mL), divinyl benzene (4 mL of 80% purity), AIBN (0.4 g), and THF (150 mL) were stirred at 60° C. under a nitrogen atmosphere for 18 hours. The solution was cooled and the solid was filtered off, rinsed in THF, then acetone, and dried in a vacuum oven at about room temperature to yield 8.1 g.

EXAMPLE 21

Poly(guanidinobutylmethacrylamide)

Poly(methacryloyl chloride) (0.5 g), agmatine sulfate (1.0 g), triethylamine (2.5 mL), and acetone (50 mL) were stirred together for 4 days. Water (100 mL) was added and the mixture stirred for 6 hours. The solid was filtered off and washed by resuspending in water (500 mL), stirring for 30 minutes, and filtering off the solid. The wash was repeated twice in water, once in methanol, and the solid was dried in a vacuum oven at about room temperature to yield 0.41 g.

EXAMPLE 22

Poly(guanidinoacrylamide)

The procedure for poly-(guanidinobutylacrylamide) was followed substituting aminoguanidine bicarbonate (5.0 g) for the agmatine sulfate, yielding 0.75 g.

EXAMPLE 23

Poly(PEH/EPI)

Epichlorohydrin (1.5 g) was added dropwise to a solution containing pentaethylenehexamine (PEH) (20 g) and water (100 mL), keeping the temperature at 65° C. The solution was stirred until it gelled and heating was continued for 4 hours (at 65° C.). After sitting overnight at room temperature the gel was removed and blended with water (1 L). The solid was filtered off, water was added (1 L), and the blending and filtration were repeated. The gel was suspended in isopropanol and the resulting solid was collected by filtration and dried in a vacuum oven at about room temperature to yield 28.2 g.

EXAMPLE 24

Ethylidenebisacetamide

Acetamide (118 g), acetaldehyde (44.06 g), glucose acetate (0.2 g), and water (300 mL) were placed in a 1 L three-neck flask fitted with condenser, thermometer, and mechanical stirred. Concentrated HCl (34 mL) was added and the mixture was heated to 45–50° C. with stirring for 24 hours. The water was then removed in vacuo to leave a thick sludge which formed crystals on cooling to 5° C. Acetone (200 mL) was added and stirred for a few minutes after which the solid was filtered off and discarded. The acetone was cooled to 0° C. and solid was filtered off. This solid was rinsed in 500 mL acetone and air dried 18 hours at about room temperature to yield 31.5 g.

EXAMPLE 25

Vinylacetamide

Ethylidenebisacetamide (31.05), calcium carbonate (2 g) and Celite 541® (2 g) were placed in a 500 mL three-neck flask fitted with a thermometer, a mechanical stirrer, and a distilling head atop a Vigreaux column. The mixture was vacuum distilled at 35 mm Hg by heating the pot to 180–225° C. Only a single fraction was collected (10.8 g) which contained a large portion of acetamide in addition to the product (determined by NMR). This solid product was dissolved in isopropanol (30 mL) to form the crude solution used for polymerization.

EXAMPLE 26

Poly(vinylacetamide)

Crude vinylacetamide solution (15 mL), divinylbenzene (1 g, technical grade, 55% pure, mixed isomers), and AIBN (0.3 g) were mixed and heated to reflux under a nitrogen atmosphere for 90 minutes, forming a solid precipitate. The solution was cooled, isopropanol (50 mL) was added, and the solid was collected by centrifugation. The solid was rinsed twice in isopropanol, once in water, and dried in a vacuum oven at about room temperature to yield 0.8 g.

EXAMPLE 27

Poly(vinylamine)

Poly(vinylacetamide) (0.79 g) was placed in a 100 mL one neck flask containing water 25 mL and concentrated HCl 25 mL. The mixture was refluxed for 5 days, the solid was filtered off, rinsed once in water, twice in isopropanol, and dried in a vacuum oven to yield 0.77 g. The product of this reaction (~0.84 g) was suspended in NaOH (46 g) and water (46 g) and heated to boiling (~140° C.). Due to foaming, the temperature was reduced and maintained at ~100° C. for 2 hours. Water (100 mL) was added and the solid collected by filtration. After rinsing once in water, the solid was suspended in water (500 mL) and adjusted to pH 5 with acetic acid. The solid was again filtered off, rinsed with water, then the isopropanol, and dried in a vacuum oven at about room temperature to yield 0.51 g.

EXAMPLE 28

Poly(ethyleneimine) Salts

Polyethyleneimine (25 g dissolved in 25 g water) was dissolved in water (100 mL) and mixed with toluene (1 L). Epichlorohydrin (2.3 mL) was added and the mixture heated to 60° C. with vigorous mechanical stirring for 18 hours. The mixture was cooled and the solid filtered off, resuspended in methanol (2 L), stirred 1 hour, and collected by centrifugation. The solid was suspended in water (2 L), stirred 1 hour, filtered off, suspended in water (4 L), stirred 1 hour, and again filtered off. The solid was suspended in acetone (4 L) and stirred 15 minutes, the liquid was poured off, acetone (2 L) was added, the mixture was stirred 15 minutes, the acetone was again poured off, and the solid was dried in a vacuum oven at about room temperature to form intermediate "D".

EXAMPLE 29

Poly(ethyleneimine Sulfate A)

Intermediate "D" (1.0 g) was suspended in water (150 mL), stirred 30 minutes, and partially neutralized with sulfuric acid (1.1 g). The mixture was stirred an additional 30 minutes, the solid was filtered off, resuspended in methanol (200 mL), stirred 5 minutes, filtered off, and dried in a vacuum oven at about room temperature.

EXAMPLE 30

Poly(ethyleneimine Sulfate B)

Intermediate "D" (1.0 g) was suspended in water (150 mL), stirred 30 minutes, and partially neutralized with sulfuric acid (0.57 g). The mixture was stirred an additional 30 minutes, the solid was filtered off, resuspended in methanol (200 mL), stirred 5 minutes, filtered off, and dried in a vacuum oven at about room temperature.

EXAMPLE 31

Poly(ethyleneimine Sulfate C)

Intermediate "D" (1.0 g) was suspended in water (150 mL), stirred 30 minutes, and partially neutralized with sulfuric acid (0.28 g). The mixture was stirred an additional 30 minutes, the solid was filtered off, resuspended in methanol (200 mL), stirred 5 minutes, filtered off, and dried in a vacuum oven at about room temperature.

EXAMPLE 32

Poly(ethyleneimine Sulfate D)

Intermediate "D" (1.0 g) was suspended in water (150 mL), stirred 30 minutes, and partially neutralized with sulfuric acid (0.11 g). The mixture was stirred an additional 30 minutes, the solid was filtered off, resuspended in methanol (200 mL), stirred 5 minutes, filtered off, and dried in a vacuum oven at about room temperature.

EXAMPLE 33

Poly(ethyleneimine Tartrate A)

Intermediate "D" (1.0 g) was suspended in water (150 mL), stirred 30 minutes, and partially neutralized with tartaric acid (1.72 g). The mixture was stirred an additional 30 minutes, the solid was filtered off, resuspended in methanol (200 mL), stirred 5 minutes, filtered off, and dried in a vacuum oven at about room temperature.

EXAMPLE 34

Poly(ethyleneimine Tartrate B)

Intermediate "D" (1.0 g) was suspended in water (150 mL), stirred 30 minutes, and partially neutralized with tartaric acid (0.86 g). The mixture was stirred an additional 30 minutes, the solid was filtered off, resuspended in methanol (200 mL), stirred 5 minutes, filtered off, and dried in a vacuum oven at about room temperature.

EXAMPLE 35

Poly(ethyleneimine Tartrate C)

Intermediate "D" (1.0 g) was suspended in water (150 mL), stirred 30 minutes, and partially neutralized with tartaric acid (0.43 g). The mixture was stirred an additional 30 minutes, the solid was filtered off, resuspended in methanol (200 mL), stirred 5 minutes, filtered off, and dried in a vacuum oven at about room temperature.

EXAMPLE 36

Poly(ethyleneimine Ascorbate A)

Intermediate "D" (1.0 g) was suspended in water (150 mL), stirred 30 minutes, and partially neutralized with ascorbic acid (4.05 g). The mixture was stirred an additional 30 minutes, the solid was filtered off, resuspended in methanol (200 mL), stirred 5 minutes, filtered off, and dried in a vacuum oven at about room temperature.

EXAMPLE 37

Poly(ethyleneimine Ascorbate B)

Intermediate "D" (1.0 g) was suspended in water (150 mL), stirred 30 minutes, and partially neutralized with ascorbic acid (2.02 g). The mixture was stirred an additional 30 minutes, the solid was filtered off, resuspended in methanol (200 mL), stirred 5 minutes, filtered off, and dried in a vacuum oven at about room temperature.

EXAMPLE 38

Poly(ethyleneimine Ascorbate C)

Intermediate "D" (1.0 g) was suspended in water (150 mL), stirred 30 minutes, and partially neutralized with ascorbic acid (1.01 g). The mixture was stirred an additional 30 minutes, the solid was filtered off, resuspended in methanol (200 mL), stirred 5 minutes, filtered off, and dried in a vacuum oven at about room temperature.

EXAMPLE 39

Poly(ethyleneimine Citrate A)

Intermediate "D" (1.0 g) was suspended in water (150 mL), stirred 30 minutes, and partially neutralized with citric acid (1.47 g). The mixture was stirred an additional 30 minutes, the solid was filtered off, resuspended in methanol (200 mL), stirred 5 minutes, filtered off, and dried in a vacuum oven at about room temperature.

EXAMPLE 40

Poly(ethyleneimine Citrate B)

Intermediate "D" (1.0 g) was suspended in water (150 mL), stirred 30 minutes, and partially neutralized with citric acid (0.74 g). The mixture was stirred an additional 30 minutes, the solid was filtered off, resuspended in methanol (200 mL), stirred 5 minutes, filtered off, and dried in a vacuum oven at about room temperature.

EXAMPLE 41

Poly(ethyleneimine Citrate C)

Intermediate "D" (1.0 g) was suspended in water (150 mL), stirred 30 minutes, and partially neutralized with citric acid (0.37 g). The mixture was stirred an additional 30 minutes, the solid was filtered off, resuspended in methanol (200 mL), stirred 5 minutes, filtered off, and dried in a vacuum oven at about room temperature.

EXAMPLE 42

Poly(ethyleneimine Succinate A)

Intermediate "D" (1.0 g) was suspended in water (150 mL), stirred 30 minutes, and partially neutralized with succinic acid (1.36 g). The mixture was stirred an additional 30 minutes, the solid was filtered off, resuspended in methanol (200 mL), stirred 5 minutes, filtered off, and dried in a vacuum oven at about room temperature.

EXAMPLE 43

Poly(ethyleneimine Succinate B)

Intermediate "D" (1.0 g) was suspended in water (150 mL), stirred 30 minutes, and partially neutralized with succinic acid (0.68 g). The mixture was stirred an additional 30 minutes, the solid was filtered off, resuspended in methanol (200 mL), stirred 5 minutes, filtered off, and dried in a vacuum oven at about room temperature.

EXAMPLE 44

Poly(ethyleneimine Chloride)

Polyethyleneimine (100 g in 100 g water) was dissolved in water (640 mL additional) and the pH was adjusted to 10 with concentrated HCl. Isopropanol (1.6 L) was added, followed by epichlorohydrin (19.2 mL). The mixture was stirred under nitrogen for 18 hours at 60° C. The solids were filtered off and rinsed with methanol (300 mL) on the funnel. The solid was rinsed by resuspending it in methanol (4 L), stirring 30 minutes, and filtering off the solid. The rinse was repeated twice with methanol, followed by resuspension in water (1 gallon). The pH was adjusted to 1.0 with concentrated HCl the solid was filtered off, resuspended in water (1 gallon), the pH again adjusted to 1.0 with concentrated HCl, the mixture stirred 30 minutes, and the solid filtered off. The methanol rinse was again repeated and the solid dried in a vacuum oven at about room temperature to yield 112.4 g.

EXAMPLE 45

Poly(dimethylethyleneimine Chloride)

Poly(ethyleneimine chloride) (5.0 g) was suspended in methanol (300 mL) and sodium carbonate (50 g) was added. Methyl iodide (20 mL) was added and the mixture heated to reflux for 3 days. Water was added to reach a total volume of 500 mL, the mixture stirred for 15 minutes, and the solid filtered off. The solid was suspended in water (500 mL), stirred 30 minutes, and filtered. The solid was suspended in water (1 L), the pH adjusted to 7.0 with concentrated HCl, and the mixture stirred for 10 minutes. The solid was filtered off, resuspended in isopropanol (1 L), stirred 30 minutes, filtered off, and dried in a vacuum oven at about room temperature to yield 6.33 g.

EXAMPLE 46

Poly(methacryloyl Chloride)

Methacryloyl chloride (20 mL), divinyl benzene (4 mL of 80% purity), AIBN (0.4 g), and THF (150 mL) were stirred at 60° C. under a nitrogen atmosphere for 18 hours. The solution was cooled, and the solid was filtered off, rinsed in THF, then acetone, and dried in a vacuum oven at about room temperature to yield 8.1 g.

EXAMPLE 47

Poly(guanidinobutylmethacrylamide)

Poly(methacryloyl chloride) (0.5 g), agmatine sulfate (1.0 g), triethylamine (2.5 mL), and acetone (50 mL) were stirred together for 4 days. Water (100 mL) was added, and the mixture stirred for 6 hours. The solid was filtered off, washed by resuspending in water (500 mL), stirring for 30 minutes, and filtering off the solid. The wash was repeated twice in water, once in methanol, and the solid was dried in a vacuum oven at about room temperature to yield 0.41 g.

EXAMPLE 48

Poly(PEH/EPI)

Epichlorohydrin (21.5 g) was added dropwise to a solution containing pentaethylenehexamine (20 g) and water (100 mL), keeping the temperature below 65° C. The solution was stirred until it gelled, and heating was continued for 4 hours (at 65° C.). After sitting overnight at room temperature, the gel was removed and blended with water (1 L). The solid was filtered off, water was added (1 L), and the blending and filtration were repeated. The gel was suspended in isopropanol, and the resulting solid was collected by filtration and dried in a vacuum oven at about room temperature to yield 28.2 g.

EXAMPLE 49

Poly(TAEA-acrylamide)

Poly(NHS-acrylate) (4.4 g) was suspended in a solution containing water (100 mL) and tris(2-aminoethyl)amine (30 mL) which had been adjusted to pH 9 with concentrated HCl. After 4 days of stirring, the solid was filtered off, and the wash repeated. The solid was then rinsed briefly with water twice, isopropanol once, and dried in a vacuum oven at about room temperature to yield 3.4 g.

EXAMPLE 50

Poly(PEH-acrylamide)

Poly(NHS-acrylate) (5.0 g) was suspended in a solution containing water (100 mL) and pentaethylene hexamine (30 mL) which had been adjusted to pH 10 with concentrated HCl. After 4 days of stirring, the solid was filtered off and resuspended in water (500 mL). The mixture was stirred for 4 hours, the solid was filtered off, and the wash repeated. The solid was then rinsed briefly with water twice, isopropanol once, and dried in a vacuum oven at about room temperature to yield 4.7 g.

EXAMPLE 51

Poly(MI/EPI)

To a 500 mL flask was added 2-methylimidazole (41.00 g, 0.50 mol) and water (100 mL). The solution was heated to 55° C., and epichlorohydrin (46.3 g. 0.50 mol) was added dropwise over 100 minutes. The maximum temperature reached during the addition was 75° C. When the addition was complete, the solution was heated to 90° C. and held at that temperature for 18 hours. In the morning, the reaction was cooled to 45° C., and epichlorohydrin (8.7 g, 0.094 mol) was added dropwise. After the addition was complete, the solution was stirred at 45° C. for 2 hours. At this point, a solution of sodium hydroxide (3.78 g, 0.094 mol) in water (15 mL) was prepared. The reaction was cooled, and the sodium hydroxide solution was added dropwise at 28° C. over 10 minutes. The solution was stirred for an additional 15 minutes and then transferred to a beaker and heated to 95° C. on a hot plate. When the reaction solidified, it was placed in an oven at 125° C. for 5 hours to cure. After cooling to room temperature, the polymer was broken up and added to 2000 mL of water. The mixture was allowed to stand for 3 hours and then blended in two portions. The hydrated gel was filtered and then dehydrated with isopropanol in two steps in the blender. Filtration and vacuum drying at about room temperature afforded 83.51 g of title polymer.

EXAMPLE 52

Polyallylamine Cross-Linked with Epichlorohydrin

An aqueous solution of poly(allylamine hydrochloride) (500 lb of a 50.7% aqueous solution) was diluted with water (751 lb) and neutralized with aqueous sodium hydroxide (171 lb of a 50% aqueous solution). The solution was cooled to approximately 25° C., and acetonitrile (1340 lb) and epichlorohydrin (26.2 lb) were added. The solution was stirred vigorously for 21 hours. During this time, the reactor contents changed from two liquid phases to a slurry of particles in a liquid. The solid gel product was isolated by filtration. The gel was washed in an elutriation process with water (136,708 lb). The gel was isolated by filtration and rinsed with isopropanol. The gel was slurried with isopropanol (1269 lb) and isolated by filtration. The isopropanol/water wet gel was dried in a vacuum dryer at 60° C. The dried product was ground to pass through a 50 mesh screen to give a product suitable for pharmacologic use (166 lb, 73%).

Clinical Studies I: Observations with Renagel® (Geltex Pharmaceuticals. Inc., Waltham, Mass.)

Serum Glucose was measured as a safety laboratory in haemodialysis clinical studies, Protocols 1–6, in patients with diabetes as the primary cause of renal failure. None of the glucose measurements were fasting measurements. A description of each of clinical Protocols 1–6 may be found in the following references, the teachings of which are incorporated herein by reference in their entireties:

Protocol 1:

Chertow, G. M., Burke, S. K., Lazarus, J. M., Stenzel, K. H., Wombolt, D., Goldberg, D., Bonventre, J. V., and Slatopolsky, E., "Poly(allylamine hydrochloride) (RenaGel®): a noncalcemic phosphate binder for the treatment of hyperphosphatemia in chronic renal failure," *Am J Kid Dis.* 29: 66–71 (1997).

Protocol 2:

Goldberg, D. I., Dillon, M. A., Slatapolsky, E. A., Garrett, B., Gray, J. R., Marbury, T., Weinberg, M., Wombolt, D., and Burke, S. K., "Effect of RenaGel, a non-absorbed, calcium- and aluminum-free phosphate binder, on serum phosphorus, calcium, and intact parathyroid hormone in end-stage renal disease patients," *Nephrol Dial Transplant.* 13: 2303–2310 (1998).

Protocol 3:

Chertow, G. M., Dillon, M., Burke, S. K., Steg, M., Bleyer, A. J., Garrett, B. N., Domoto, D. T., Wilkes, B. M., Wombolt, D. G., and Slatopolsky, E., "A randomized trial of sevelamer hydrochloride (RenaGel®) with and without supplemental calcium. Strategies for the control of hyperphosphatemia in hemodialysis patients," *Clin Nephrol.* 51: 18–26 (1999).

Protocol 4:

Bleyer, A. J., Burke, S. K., Dillon, M., Garrett, B., Kant, K. S., Lynch, D., Raman, S. N., Shoenfeld, P., Teitelbaum, I., Zieg, S., and Slatopolsky, E., "A comparison of the calcium-free phosphate binder sevelamer hydrochloride with calcium acetate in the treatment of hyperphosphatemia in hemodialysis patients," *Am J Kid Dis.* 33: 694–701 (1999).

Protocol 5:

Slatopolsky, E., Burke, S. K., Dillon, M. A., and the Renagel Study Group, "RenaGel®, a nonabsorbed calcium- and aluminum-free phosphate binder, lowers serum phosphorus and parathyroid hormone," *Kid Int.* 55: 299–307 (1999).

Protocol 6:

Chertow, G. M., Burke, S. K., Dillon, M. A., and Slatopolsky, E., for the Renagel Study Group, "Long-term effects of sevelamer hydrochloride on the calcium x phosphorus product and lipid profile of haemodialysis patients," *Nephol Dial Transplant.* 14: 2907–2914 (1999).

Decreases in serum glucose from baseline to the end of the study were seen in each of the haemodialysis clinical studies (Table 1) except the clinical study of protocol 3.

TABLE 1

| Protocol | Baseline mg/dL | Endpoint | Change | P-Value |
|---|---|---|---|---|
| 1 | 179.50 | 130.39 | −37.9 | 0.0984 |
| 2 | 135.1 | 132.6 | −2.8 | 0.7903 |
| 3 | 146.9 | 154.6 | 18.4 | 0.9063 |
| 4 | 135.3 | 128.7 | −6.7 | 0.1327 |
| 5 | 127.1 | 121.5 | −3.7 | 0.3203 |
| 6 | 135.1 | 235.4 | −9.7 | 0.1405 |

Clinical Studies II: Observations with Colesevelam

Glucose was measured as a safety laboratory at weeks −4, 0, 12 and 24. There was a significant group effect for serum glucose (p=0.03) for change from day 0 to 168 for all patients. Decreases from day 0 to 168 of 2.8 and 2.2 mg/dL in the 3.8 and 4.5 g/d groups were statistically significant (p<0.01).

Cholestyramine (8 g/d, bid) improved glycemic control in patients with Type II diabetes, possibly related to changes in glucose absorption. In the pivotal trial, plasma glucose decreased in the two high dose colesevelam groups. In a post hoc analysis of patients with diabetes (n=13), serum glucose fell from 140 mg/dL on diet alone to 122 mg/dL on colesevelam 3.8 or 4.5 g/d (p<0.01). Similar effects were seen in an analysis of the integrated safety data. Confirmatory studies that could be done inexpensively on stored sera (from drug interaction studies) include (1) measurements of HgbA1c in the pivotal 24 week trial; and (2) measurements of glucose and insulin response to a standard meal with or without colesevelam.

EQUIVALENTS

It should be understood, however, that the foregoing description of the invention is intended merely to be illustrative by way of example only and that other modifications, embodiments, and equivalents may be apparent to those skilled in the art without departing from its spirit.

While this invention has been particularly shown and described with references to preferred embodiments thereof, it will be understood by those skilled in the art that various changes in form and details may be made therein without departing from the scope of the invention encompassed by the appended claims.

What is claimed is:

1. A method for reducing serum glucose levels in a human diabetic patient in need thereof, comprising administering to said patient a therapeutically effective amount of colesevelam or a pharmaceutically acceptable salt thereof.

2. A method for reducing serum glucose levels in a human diabetic patient in need thereof, comprising administering to said patient a therapeutically effective amount of colesevelam or a pharmaceutically acceptable salt thereof, wherein said colesevelam or pharmaceutically acceptable salt thereof is the only active ingredient administered to the patient.

3. The method of claim 1, wherein a pharmaceutically acceptable salt of colesevelam is administered to the patient.

4. The method of claim 2, wherein a pharmaceutically acceptable salt of colesevelam is administered to the patient.

* * * * *